United States Patent [19]

Van Ness

[11] Patent Number: 5,232,830
[45] Date of Patent: Aug. 3, 1993

[54] INTRINSIC FLUORESCENT QUENCHING METHODS

[75] Inventor: Jeffrey Van Ness, Bothell, Wash.

[73] Assignee: MicroProbe Corporation, Bothell, Wash.

[21] Appl. No.: 558,967

[22] Filed: Jul. 26, 1990

Related U.S. Application Data

[63] Continuation-in-part of Ser. No. 522,442, May 11, 1990.

[51] Int. Cl.$^5$ .......................... C12Q 1/68; C12Q 1/25; C12Q 1/42; C12Q 1/28
[52] U.S. Cl. ............................................ 435/6; 435/4; 435/7.1; 435/14; 435/21; 435/28; 435/800; 436/501; 436/588; 536/23.1
[58] Field of Search ................... 435/4, 6, 7.1, 7.9, 435/14, 21, 28; 436/501, 531, 546, 528; 536/27, 23.1

[56] References Cited

U.S. PATENT DOCUMENTS

| | | | |
|---|---|---|---|
| 4,391,904 | 7/1983 | Litman et al. | 435/7 |
| 4,486,539 | 12/1984 | Ranki et al. | 435/6 |
| 4,563,419 | 1/1986 | Ranki et al. | 436/504 |
| 4,615,985 | 10/1986 | Deutsch et al. | 436/531 |
| 4,654,300 | 3/1987 | Zuk et al. | 435/7 |

OTHER PUBLICATIONS

Dunn et al., Cell 12:23–26 (1977).
Miller et al., Clin. Chem. 30:1467–1472 (1984).
Brown et al., Clin. Chem. 31:1500–1505 (1985).
Kobayashi et al., Steroids 36:177–183 (1980).
Hemmilä, Clin. Chem. 31:359–370 (1985).

*Primary Examiner*—Johnnie R. Brown
*Assistant Examiner*—Gary L. Kunz
*Attorney, Agent, or Firm*—Townsend and Townsend Khourie and Crew

[57] ABSTRACT

Novel methods and compositions for detecting a member of a ligand pair on solid supports having intrinsic fluorescence are disclosed. A target member of a ligand pair is contacted with a capture member of a ligand pair, wherein the capture member is immobilized on a solid support having intrinsic fluorescence, and the contacted pair is in association with a colorimetric reporter, then the solid support is irradiated the solid support, and the resultant fluorescence is determined. Preferably, methods include hybridization assays of nucleic acid sequences on such solid supports. The extent of detecting a member of a ligand pair, preferably a nucleic acid sequence, is determined using a method or technique described throughout this document as fluorescent quenching. Methods and compositions pertaining to solid supports having their intrinsic or natural fluorescence quenched or masked are also described herein. The present invention has utility in detection assays for a member of a ligand pair. Such ligand pairs include, but are not limited to, antigens (or epitopes) and appropriate antibodies, complementary nucleic acid sequences, hormones and their receptors, enzymes and corresponding inhibitors, lectins and sugars, etc.

18 Claims, No Drawings

INTRINSIC FLUORESCENT QUENCHING METHODS

CROSS REFERENCE TO RELATED APPLICATIONS

This application is a continuation-in-part of U.S. Ser. No. 07/522,442, filed May 11, 1990 (assigned to the assignee of the present application and incorporated herein by reference).

BACKGROUND OF THE INVENTION

The present invention relates generally to the field of detection assays and, more particularly, to fluorescent quenching methods and compositions for quantifying the extent of ligand pair binding on solid supports, for example those employed in nucleic acid hybridizations.

Nucleic acid hybridization is a known method for identifying specific sequences of nucleic acids. Hybridization is based upon base pairing between complementary nucleic acid strands. When single stranded nucleic acids are incubated in appropriate buffer solutions, complementary base sequences pair to form double stranded stable molecules. The presence or absence of such pairing may be detected by several different methods described in the art.

Hybridization assays generally involve multiple steps, for example the hybridization technique described by Dunn, et al., Cell 12:23-36 (1977) (incorporated herein by reference), wherein a sandwich-type assay consists of a first hybridization between a "target" nucleic acid and a "capture" nucleic acid probe that has been immobilized on a solid support and a second hybridization between a "signal" nucleic acid probe, typically labeled with a radioactive isotope, and a different region of the immobilized target nucleic acid. The hybridization of the signal probe may then be detected by, for example, autoradiography.

Ranki, et al., U.S. Pat. No. 4,486,539 and U.S. Pat. No. 4,563,419 (both patents incorporated herein by reference), describe sandwich-type assays that first require steps to render nucleic acids single stranded before the single stranded nucleic acids are allowed to hybridize with a nucleic acid affixed to a solid carrier and with a nucleic acid labeled with a radioisotope.

Litman, et al., U.S. Pat. No. 4,391,904 (incorporated herein by reference), describes test strip kits wherein a member of an immunological pair is bonded to a solid surface. Also, Miller, et al., Clin. Chem. 30:1467-1472 (1984), and Brown, et al., Clin. Chem. 31:1500-1505 (1985) (both articles incorporated herein by reference), describe an analytical test chamber containing cellulose threads coupled to an antibody as a solid matrix that permits multiple test results from a single sample.

An indirect quenching fluoroimmunoassay, double receptor fluoroimmunoassay, and protection fluoroimmunoassay represent assay formats in which antibodies are typically directed against the fluorescer. The assay is based on competition for the labeled antigen by the analyte-specific antibody and by the antibody directed against the fluorescer. See Hemmilä, Clin. Chem. 31:359-370 (1985) (incorporated herein by reference) for a review of fluoroimmunoassays and immunofluorometric assays. See also Kobayashi, Steroids 36:177-183 (1980) (fluorescence quenching immunoassay of serum cortisol) (incorporated herein by reference).

Zuk, et al., U.S. Pat. No. 4,654,300 describes an immunoassay having conjugated fluorescent particles and conjugated catalyst wherein the particles and catalysts are conjugated to members of a specific binding pair.

SUMMARY OF THE INVENTION

The present invention comprises novel methods and compositions for detecting a member of a ligand pair on solid supports having intrinsic fluorescence. Such methods include the steps of contacting a target member of a ligand pair with a capture member of the ligand pair, wherein the capture member is immobilized on a solid support having intrinsic fluorescence, and the contacted pair is in association with a colorimetric reporter; irradiating the solid support, wherein the solid support is attached to the ligand pair in association with the colorimetric reporter; and determining the resultant fluorescence.

In particular, hybridization assays of nucleic acid sequences on such solid supports is described. Herein, a target nucleic acid and a complementary capture nucleic acid probe are contacted, wherein the capture probe is immobilized on a solid support having intrinsic fluorescence, preferably nylon beads, and the contacted target nucleic acid-capture probe complex is in association with a colorimetric reporter; irradiating the solid support, wherein the solid support is attached to the hybridized capture probe-target nucleic acid complex; and determining the resultant fluorescence. The extent of detecting a member of a ligand pair, preferably a nucleic acid sequence, is determined using a method or technique described throughout this document as fluorescent quenching.

Fluorescent quenching employs the use of a solid support, preferably a nylon bead, that fluoresces when irradiated with ultraviolet light (e.g., 240 to 750 nanometers (nm)). A colorimetric reporter, such as a preferred insoluble enzymatic product, which is deposited on the solid support, quenches the fluorescence of the solid support and yields a means to quantify the product, preferably using commercially available fluorometers. The solid supports described herein do not require the use of a plurality of fluorescent chromophoric groups bound to the surface of the solid support, but rather rely on the intrinsic or natural fluorescence of the polymeric material comprising the solid support. The irradiation and detection of fluorescence is also not dependent on the use of narrow or specific wavelengths of ultraviolet light.

Also disclosed here are methods and compositions pertaining to solid supports, preferably nylon or other polymeric beads, having their intrinsic or natural fluorescence quenched or masked, preferably with commercially available dyes. Fluorescent products, preferably enzymatic products, can be measured directly in the presence of the solid support using most types of fluorometers.

Methods and compositions of the present invention have utility in detection assays for a member of a ligand pair. Such ligand pairs include, but are not limited to, antigens (or epitopes) and appropriate antibodies, complementary nucleic acid sequences, hormones and their receptors, enzymes and corresponding inhibitors, lectins and sugars, etc.

DETAILED DESCRIPTION OF THE INVENTION AND PREFERRED EMBODIMENTS

The present invention includes methods and compositions useful for the detection of a member of a ligand pair. As used herein, a member of a ligand pair includes any compound or composition for which an antiligand (or receptor) exists or can be prepared. An antiligand represents the corresponding member of the ligand pair and can be defined to include any compound or composition capable of recognizing, or having an affinity for, a particular ligand. Examples include, but are not limited to, antigens (or epitopes) and appropriate antibodies, complementary nucleic acid sequences, hormones and their receptors, enzymes and corresponding inhibitors, lectins and sugars, etc.

The terms "capture member of a ligand pair" and "target member of a ligand pair" refer to, respectively, the known or utilized ligand member and the antiligand member to be detected. Another term used herein for the target member or antiligand is the analyte, defined as the compound or composition to be detected and preferably measured.

The term "solid support" refers to any surface that is transferable from solution to solution or forms a structure for conducting detection assays, and includes beads, membranes, microtiter wells, strings, plastic strips, or any surface onto which a member of a ligand pair may be immobilized. As used herein, "bead" encompasses any type of solid or hollow sphere, ball, bearing, cylinder, or other similar configuration composed of plastic, ceramic, metal, or polymeric material onto which a member of a ligand pair may be immobilized. As such, the term also includes nylon string or strings.

The solid support must possess some type of fluorescence that can be measured. Fluorescence is defined as a substance's capability for energy or radiation absorption at a certain wavelength spectrum, which results in electron excitation to a higher state and then spontaneous decay and emission of detectable radiation at a longer wavelength. This fluorescence can be intrinsic or inherent in the material comprising the solid support, or fluorescent compounds can be bound (either covalently or noncovalently) to the solid support during manufacturing or derivation process. The latter compounds can include, but are not limited to, commercially available fluorescein, Texas Red, rhodamine, and the like. In a preferred embodiment of the present invention, native (i.e., unaltered white) nylon beads are employed, as these solid supports have an intrinsic fluorescence.

Preferred materials for the present solid supports include materials selected from the group consisting of nylons, polyethylene, polyvinylchloride, polystyrene, polypropylene, acrylonitrile butadiene styrene (ABS), acrylics, acetals, polycarbonates, fluoroplastics, polyesters, phenolics, amino resins, epoxies, polyurethane, and silicones. Preferably, a nylon bead that is spherical in shape is employed in the present invention, and a preferred bead has a diameter range from about 0.01 inch to about 0.5 inch, more preferably from about 0.06 inch to about 0.09 inch (corresponding to commercially available 3/32 inch nylon beads), and most preferably about 0.09 inch (corresponding to commercially available 3/32 inch nylon beads). Additionally, it is preferred that such nylon beads are unpolished.

In the methods of the present invention, a target member of a ligand pair is contacted with a capture member of the ligand pair under suitable conditions. Such conditions vary depending upon the ligand pair selected and are known to those of ordinary skill in the art. Contacting refers to binding of the target member and the capture member, whereby a stable complex is formed.

If complementary nucleic acid sequences are chosen, suitable conditions are those resulting in hybridization, see Hames, B. D., et al. (ed.), Nucleic Acid Hybridization, A Practical Approach, IRL Press, New York (1985) (incorporated herein by reference).

The capture member of the ligand pair is immobilized on a solid support having intrinsic fluorescence. The contacted ligand pair is in association with a colorimetric reporter, wherein a reporter generates a measurable signal and a colorimetric reporter is defined as a compound or composition capable of giving rise to a product that can absorb radiation, or a compound or composition itself capable of absorbing radiation, and also capable of masking or quenching the fluorescence of the solid support.

Preferred colorimetric reporters are enzymes capable of producing and depositing an insoluble colorimetric product on the solid support where it can be detected and measured. Such enzymes include, but are not limited to, horseradish peroxidase (HRP), alkaline phosphatase (AP), $\beta$-galactosidase, and the like. Representative substrates for each of these preferred enzymes include 4-methoxynapthol(4 MN), 5-bromo-4-chloroindoyl-3-phosphate/nitroBlue tetrazolium (NBT), and o-nitrophenyl-beta-D-galactopyranoside, respectively.

Once the immobilized ligand pair is formed, the solid support is irradiated, preferably with an ultraviolet light source (about 240 nm to about 750 nm). If the colorimetric reporter is a preferred enzyme, substrate appropriate to that enzyme is added, and the substrate is thereby converted to enzymatic products on the solid support, and then the solid support is irradiated. The resultant fluorescence is determined, preferably quantitatively and with a fluorometer. Alternatively, the solid support may be photographed during irradiation or visually inspected under an appropriate light source or determined by other such qualitative means.

The intensity of the measured fluorescence is inversely proportional to the quantity of preferred enzymatic product deposited on the solid support, and the quantity of enzymatic product is directly proportional to the quantity of bound analyte (antiligand). Because the quantity of preferred enzymatic product produced is proportional to the quantity of bound analyte (antiligand) and the quenching of fluorescence by the colored enzymatic product is proportional to the quantity of product produced, the present methods allow quantitative determination of bound analyte. In many cases, the relation between bound analyte and fluorescence quenching is linear.

One advantage of these methods, which provide for the measurement of color, is that any configuration of solid support can be utilized, including configurations in which it is difficult to obtain reflectance or transmission measurements. Such configurations include, for example, strings, spheres, and amorphous shapes. Another advantage is that the quenching is nearly independent of the color of the enzymatic product and therefore removes the necessity of changing wavelength parameters of excitation and emission filters of fluorometers when different enzymatic systems are employed. This advantage is usually lacking for visible light-based reflectance or transmission measurement systems that must be designed for specific colors or compounds.

In a preferred embodiment, the present methods are employed in nucleic acid hybridizations for detection of particular sequences. Nucleic acids include deoxyribonucleic acid (DNA) and ribonucleic acid (RNA). In a more preferred embodiment, a sandwich assay is employed. A target nucleic acid and a complementary capture nucleic acid probe, wherein the capture probe is immobilized on a solid support having intrinsic fluorescence, are contacted under suitable conditions for hybridization, Hames, B. D., et al. (ed.), Nucleic Acid Hybridization, A Practical Approach, IRL Press, New York (1985) (incorporated herein by reference).

It is preferred that the solid supports having intrinsic fluorescence be covalently coated with a polymer, such as poly(ethyleneimine). The polymer-coated solid supports are then conjugated with activated oligonucleotides using chemistries similar to, or the same as, those described below. As used herein, oligonucleotides refer to short nucleic acid sequences that are approximately 10 to 100 bases in length. Activated oligonucleotides refer in general to oligonucleotides that have been reacted with a chemical compound and rendered chemically active. Such oligonucleotides can be used as capture probes in hybridization assays and are preferably chemically synthesized using commercially available methods and equipment. For example, the solid phase phosphoramidite method can be used to produce short probes of between 15 and 50 bases having a molecular weight of less than 16,000 daltons. For the synthesis of oligonucleotides, see Caruthers, et al., Cold Spring Harbour Symp. Quant. Biol. 47:411–418 (1982); Adams, et al., J. Am. Chem. Soc. 105:661 (1983) (both are incorporated herein by reference).

When synthesizing an capture oligonucleotide probe for a specific target nucleic acid, the choice of nucleotide sequence will determine the specificity of the test. For example, by comparing DNA sequences from several bacterial isolates, one can select a sequence for bacterial detection that is either type-specific or genus-specific. Comparisons of DNA regions and sequences can be achieved using commercially available computer programs.

The preferred capture oligonucleotide probes for use in the present invention are synthetic oligonucleotides from about 20 to about 100 bases in length. A spacer (linker) arm, i.e., a chemical moiety that extends or links other chemical groups, and preferably is a carbon chain containing from about 2 to about 12 carbon atoms, more preferably about 6 carbon atoms, containing a blocked amine group can be coupled during synthesis using conventional chemistry to the 5'-hydroxyl group of an oligonucleotide. A primary amine is the preferred group for attachment to monofunctional or multifunctional reagents, and its attachment via a hexyl arm is preferred. The reagents for the attachment of primary spacer arms terminating in a primary amine are commercially available. Starting materials suitable for use in the present invention are described in PCT 86/01290; Nucl. Acids Res. 15:3131 (1987); Nucl. Acids Res. 15:2891 (1987); and Nucl. Acids Res. 14:7985 (1986) (all incorporated herein by reference).

The selected oligonucleotides are then activated with a monofunctional or multifunctional reagent. Such a reagent includes, but is not limited to, homotrifunctional, heterotrifunctional, homobifunctional, and heterobifunctional reagents, and such oligonucleotides may be linked to the polymer-coated solid supports according to the following chemistries. An amine-tailed oligonucleotide can be activated with a monofunctional or multifunctional reagent, for example cyanuric chloride whereby an alkylamino dichlorotriazine is formed, which is then reactive toward the amine-containing polymer.

Although cyanuric chloride, a homotrifunctional reagent is preferred, other reagents can be used. For example, N-succinimidyl-4-(iodoacetamido)-benzoate (SIAB) is a heterobifunctional reagent, and disuccinimidyl suberate is a homobifunctional reagent. If carboxyl groups are involved, the heterobifunctional reagent, 1-ethyl-3-(dimethylaminopropyl)-carbodiimide can be used. Other similar monofunctional and multifunctional (heteromultifunctional and homomultifunctional) reagents are can be used.

Target nucleic acid analyte (antiligand) is usually a polynucleotide with an average length from about 20 to about 20,000 bases in length. Suitable conditions for hybridization refer to stringent conditions wherein base-pairing mismatching does not occur and the hybridized product is perfectly base-paired.

The contacted target nucleic acid-capture probe complex is then hybridized to a signal probe wherein the signal probe is complementary to the target and is labeled with a colorimetric reporter. Alternatively, this step can be performed simultaneously with the capture of the target by including the signal probe within, for example, the hybridization solution.

In a preferred embodiment, the signal probe is labeled with biotin or streptavidin. If an enzyme is selected as the reporter group, it may be linked to the signal probe through a biotin-streptavidin complex. More preferably, the signal probe is biotinylated and the reporter enzyme is conjugated to streptavidin. After introduction of an appropriate substrate, the insoluble enzymatic product is then allowed to deposit or accumulate on the surface of the bead. This above-described assay produces a complex of the form capture probe:target nucleic acid:signal probe, constituting a sandwich assay. As with the previously discussed methods, the solid support is then irradiated and fluorescence is determined.

The particular hybridization technique is not essential to the invention and one of ordinary skill in the art will appreciate the variety of such techniques. Hybridization techniques are generally described in Hames, B. D., et al. (ed.), Nucleic Acid Hybridization, A Practical Approach, IRL Press, New York (1985) (incorporated herein by reference). As improvements are made in hybridization techniques, they can readily be applied to the present invention.

The present invention also includes compositions and methods that permit the direct determination or quantification of a fluorescent product, preferably an enzymatic product such as those listed above, in the presence of the solid support. Fluorescence-based assays have been widely employed in diagnostics as fluorescent substrates are generally 10 to 1000 times more sensitive than respective colorimetric enzymatic products.

However, the fluorescent product must be measured in an environment that neither quenches the product nor is fluorescent itself. Because the solid supports described herein possess a very high intrinsic fluorescence in their native state, it is not possible to accurately measure a fluorescent product in the presence of these solid supports. The solid support must therefore be removed from the substrate solution or the solution decanted and placed in a separate vesicle to allow accurate determination of fluorescence.

To alleviate such problems, the present invention includes compositions suitable for ligand pair detection comprising a solid support having its intrinsic fluorescence quenched. The native color of the solid support is masked. In the case of nylon beads, the native color is usually white. Preferably, masking is performed with a dye of any color, whereby the intrinsic fluorescence is substantially reduced or quenched. A minimum 10-fold reduction in fluorescence is preferred, although this is varies with the size of the preferred nylon bead. The reduction in fluorescence permits the solid support to be present during the measurement of fluorescence of the preferably enzymatic product and alleviates the need to transfer solutions or solid supports.

Preferably, a commercially available nylon bead is used, more preferably a nylon bead having a diameter range from about 0.01 inch to about 0.5 inch, and most preferably about 0.09 inch (corresponding to 3/32 inch bead). Such a bead possesses an intrinsic fluorescence of 2000 relative fluorescence units (RFUs) when irradiated with a wavelength of 360 nm and emission can be measured at 450 nm with a 40 watt xenon lamp source. A typical fluorescence-based assay utilizing alkaline phosphatase and 4-methyl-umbelliferone phosphate will produce a soluble product possessing 8000 RFUs with saturating quantities of analyte (antiligand) and 10 to 50 RFUs at low analyte concentrations.

Therefore, the fluorescence of the solid support should be reduced from 2000 RFUs (intrinsic fluorescence) to 5 to 10 RFUs for the solid support to be present in a vesicle during fluorescence measurements. In addition, the bead-to-bead or solid support-to-solid support fluorescence should be uniform, and the standard deviation of the bead-to-bead intrinsic fluorescence should not exceed the standard deviation of the assay (typically 1 to 10%) or the measurement system (typically 1 to 5%) in order to fully utilize the potential of the fluorescent substrate.

Any selected color of dichlorotriazine, azo, or other permanent dyes will reduce the intrinsic fluorescence of the nylon bead approximately 500-fold. The dye can be of almost any color (black, blue, red, green, yellow, purple, orange, etc.), with the only requirement being that the dye not fluoresce at the same wavelength as the fluorescent product. Dark shades of colors are preferable.

The present compositions are suitable for ligand pair detection when used in methods for detecting a member of a ligand pair wherein a fluorescent reporter is employed. Fluorescent reporters are those reporters that, when irradiated, emit a fluorescent signal (wherein fluorescent is as defined above). In one embodiment, a preferred substrate is 4-methyl-umbelliferone phosphate (4-hydroxymethyl coumarin), yielding the enzymatic product, 4-methylumbelliferone, which can be used as a fluorescent reporter. For a review of fluoroimmunoassays and immunofluorometric assays, see Hemmilä, Clin. Chem. 31:359–370 (1985) (incorporated herein by reference).

Masking the intrinsic fluorescence of a solid support also permits the development of solid supports with different capture members of ligand pairs, for example oligonucleotide probes, which are then distinguishable by color. The ability to distinguish different solid supports by color has advantages, for example, in quality control in which solid supports possessing different specificities can be identified and distinguished. Also, a means is provided for achieving a maximum contrast of, for example, colorimetric enzymatic product and the surface of the solid support, thereby allowing a greater level of sensitivity when assay results are determined by visual inspection.

It is to be understood that the above description and the following Experimental section are intended to be illustrative and not restrictive. Many variations and applications will be readily apparent to one of ordinary skill in the art upon reviewing this disclosure.

In the Experimental section below, Example 1 describes the quantification of horseradish peroxidase insoluble product on 3/32 inch nylon beads using the fluorescence quenching technique. Example 2 describes the quantification of alkaline phosphatase insoluble product on 3/32 inch nylon beads using the fluorescence quenching technique. Example 3 demonstrates the ability of determining fluorescence of 4-methyl-umbelliferone in the presence of a solid support. Example 4 describes the reduction in fluorescence of nylon beads by dying the beads with different colors.

The following Materials and Procedures section pertains to Examples 1–4.

Materials

APB buffer is 0.18M NaCl, 0.05M Tris-HCl pH=7.6, 5 mM EDTA, and 0.5% Tween 20.

TMNZ buffer is 0.05M Tris pH=9.5, 1 mM $MgCl_2$, 0.5 mM $ZnCl_2$.

FW (filter wash) is 0.09M sodium chloride, 50 mM Tris pH 7.6, 25 mM EDTA.

SDS/FW is FW and 0.1% sodium dodecyl sulfate (SDS).

HRP (horseradish peroxidase) substrate solution is 0.1M sodium citrate pH 6.5, 0.2M NaPhosphate, 0.5 mg/ml.

4-methoxy-1-naphthol, 0.02 mg/ml 3-methyl-2-benzothiazolinone hydrazone and 0.0135% hydrogen peroxide.

AP (alkaline phosphatase) substrate solution is 1 mM 5-bromo-4-chloroindoyl-3-phosphate, 1 mM nitroBlue tetrazolium, and 0.01% Tween 20 in TMNZ.

Lysis and hybridization solution is 3M guanidinium thiocyanate, 2% N-lauroylsarcosine (sarcosyl), 50 mM Tris pH 7.6, 25 mM EDTA.

CAP buffer is 0.1M NaCitrate pH=6.5 and 0.2M NaPhosphate.

The fluorescent substrate for alkaline phosphatase is 0.02 mM 4-methyl-umbelliferone phosphate, 0.05M Tris pH=9.5, 1 mM $MgCl_2$, 0.5 mM $ZnCl_2$.

Oligonucleotide sequences:
Bg1: 5'-XCAATACTCGTATCGCCCGTTATTC-3'
Aa004: 5'-XACCCATCTCTGACTTCTTCTTCGG-3'
Bg016: 5'-XTACTCGTATCGCCCGTTATTCCCG-3'
Ek007: 5'-XAAAAGTGGTATTAGCACTTCCCTT-3'
PA005: 5'-XGACATACCTTCCACCATCTGCAAG-3'
PA505: 5'-XCTTGCAGATGGTGGAAGGTATCTC-3'
UP9A: 5'-XCTGCTGCCTCCCGTAGGAGT-3'

UP007: 5'-XGTATTACCGCGGCTGCTG-3'

Poly(ethyleneimine) was purchased from Polysciences (Warrington, Pa.).

Burnished or unpolished native nylon beads were purchased from Precision Ball Company (Chicago, Ill.) and The Hoover Group (Sault St. Marie, Mich.)

Triethyloxonium tetrafluoroborate, hexanediamine, phenylenediamine, succinic anhydride, N-methyl-pyrrolidinone (N-methyl-pyrrolidone, m-pyrol), Cibacron Brilliant Red, Cibacron Brilliant Yellow, Mordant Orange, Fast Blue BB, Reactive Blue 2, Mordant Brown 4, and Reactive Black were purchased from Aldrich Chemical (Milwaukee, Ill.).

N-succinimidyl-4-(iodoacetamido)-benzoate (SIAB) and Tween 20 was purchased from Pierce (Rockford, Ill.).

Guanidium isothioscyanate (GuSCN) was purchased form Kodak (Rochester, N.Y.).

Procedures

Oligonucleotide synthesis

Oligonucleotides complementary to regions conserved or hypervariable regions of the 16S-ribosomal RNA of either Actinobacillus actinomycetemcomitans (Aa), Bacteroides gingivalis (Bg), Bacteroides intermedius (Bi), Eikenella corrodens (Ek), Fusobacterium nucleatum (Fn), or Wolinella recta (Wr) were synthesized using phosphoramidite chemistry on either an ABI 380B or a Milligen 7500 automated DNA synthesizer. The oligonucleotides were prepared using the standard phosphoramidite chemistry supplied by the vendor or the H-phosphonate chemistry. Appropriately blocked dA, dG, dC, and T phosphoramidites are commercially available in these forms, and synthetic nucleosides may readily be converted to the appropriate form. Oligonucleotides were purified by adaptations of standard methods. Oligonucleotides with 5'-trityl groups were chromatographed on HPLC using a 12 $\mu$m, 300 Å Rainin (Woburn, Mass.) Dynamax C-8 4.2×250 mm reverse phase column using a gradient of 15% to 55% MeCN in 0.1N Et$_3$NH$^+$OAc$^-$, pH 7.0, over 20 min. When detritylation was performed, the oligonucleotides were further purified by gel exclusion chromatography. Analytical checks for the quality of the oligonucleotides were conducted with a Toso-Haas DEAE-NPR column at alkaline pH and by polyacrylamide gel electrophoresis (PAGE).

Preparation of the polymer-coated nylon bead 25,000 3/32 inch diameter unpolished nylon beads were placed in a flask containing 1800 ml of 100% anhydrous n-methyl-pyrrolidinone and mixed for 5 minutes at ambient temperature. 200 $\mu$l of 1 molar triethyloxonium tetrafluoroborate in dichloromethane was added and the mixture was stirred for 30 minutes at ambient temperature. The beads were then decanted and washed quickly with 4,500 ml changes of 100% n-methyl-pyrrolidinone. The beads were then transferred to a solution consisting of 3% w/v 10,000 MW poly(ethyleneimine), prepared from a 30% aqueous solution of poly(ethyleneimine), in n-methyl-pyrrolidone and stirred for 12 to 24 hours at ambient temperature. The beads were washed with 2000 ml n-methyl-pyrrolidone, 100 ml SDS/FW and finally 10×2 liter distilled water. Beads were then dried under a high vacuum for 4 to 5 hours without the use of heat. The amine content of the beads was determined by reaction with picyrlsulfonic acid.

Preparation of cyanuric chloride-derived oligonucleotides 10 to 1000 $\mu$g of 5'-amine-linked oligonucleotide were reacted with an excess of recrystallized cyanuric chloride in 10% n-methyl-pyrrolidone in an alkaline buffer (pH 8.3 to 8.5, preferably) at 19° to 25° C. for 30 to 120 minutes. The final reaction conditions consisted of 0.15M sodium borate at pH 8.3, 2 mg/ml recrystallized cyanuric chloride and 500 ug/ml respective aminohexyl oligonucleotide. The unreacted cyanuric chloride was removed by size exclusion chromatography on a G-50 Sephadex TM (Pharmacia, Uppsala, Sweden) column.

Cyanuric chloride derived oligonucleotides and poly(ethyleneimine) coated nylon beads described above were placed in a volume of 0.1M sodium borate pH 8.3 equal to the volume of the beads at 4° C. The purified cyanuric chloride derived oligonucleotide was then added to the beads, and the mixture was vigorously agitated at ambient temperature (19° to 23° C.) for 60 minutes. The beads were then washed twice with 0.1M sodium borate pH 8.3. Succinic anhydride was then added at a concentration of 10 mg/ml in 90% N-methylpyrrolidone, 10% 1M sodium borate pH 8.3 with a volume three times that the volume of the beads. The reaction was allowed to proceed for 1 hour at ambient temperature. The beads were then washed 3 times with 250 ml of 100% N-methyl-pyrrolidone, twice with distilled water, 5 times with 250 ml SDS/FW and then 4 times with 1 liter of distilled water. Beads were stored dry or in 25 mM EDTA. Radioactivity per bead was determined by liquid scintillation counting.

Lysis of bacteria and hybridization conditions

1×10$^8$ cells of Bacteroides gingivalis (Bg) were lysed in 100 $\mu$L of lysis solution at 19° C. The cell lysate was then heated in an 65 degree water bath for 10 minutes. Biotinylated probe was added to the lysate solution and to the diluent (GuSCN lysis solution) to a final concentration of 100 ng/mL, and 5 to 8 5-fold serial dilutions were made of the starting lysate. The solutions were then incubated with the derived nylon beads that had been covalently immobilized with 0.1 $\mu$g of respective oligonucleotide probe (capture probe) for 1 hour at ambient temperature with mild agitation. The solid supports were then washed once with the lysis and hybridization solution, once with FW, and once with SDS/FW. Streptavidin/HRP conjugate was added to a final concentration of 1 microgram/ml (based on streptavidin) in SDS/FW and incubated 10 to 15 minutes at ambient temperature with mild agitation. The beads were then washed three times with SDS/FW and then once with CAP buffer. 4-methoxy-naphthol substrate solution described above was added, and the reaction was allowed to proceed for 15 minutes at ambient temperature. The beads were then quickly washed once with SDS/FW and then once with FW and allowed to air dry in the dark.

Quantitative determination of the extent of hybridization (capture of target nucleic acid) using insoluble substrates for either horseradish peroxidase or alkaline phosphatase After the completion of the sandwich assay on the solid support, herein 3/32 inch nylon beads, and the deposition of the insoluble substrate product onto the surface of the bead described above for either HRP or alkaline phosphatase, the quantity of target captured was determined by fluorescence quenching. The beads were dried for 15 to 30 minutes at ambient temperature and then individually placed in an opaque white, round-bottom, microtiter plate (Dynatek Laboratories, Chantilly, Va.). The beads were read using a fluorometer (Fluoroskan II, Flow Laboratories, McLean, Va.) in which excitation was at 584 nanometers and emission was at 612 nanometers. The beads possessed an intrinsic fluorescence of about 800 RFUs, and the presence of the colorimetric substrate product effectively quenched the intrinsic fluorescence. The lower the indicated fluorescence correlated with the greater the quantity of captured target nucleic acid.

EXAMPLE 1

Example 1 describes the quantification of signal obtained in a typical sandwich assay format in which a target nucleic acid sequence is sequestered and then detected using a colorimetric insoluble enzymatic product obtained with a horseradish peroxidase system.

3M GnSCN lysis solution was used to lyse $1 \times 10^8$ Bacteroides gingivalis (Bg) cells in 100 microliter volumes at 19° C. The lysate was then heated to 65° C. for 5 minutes. A biotinylated 24-mer oligonucleotide probe complementary to conserved regions of bacterial 16 s rRNA (UP9A signal probe) was added to a final concentration of 100 nanograms per ml.

3-fold serial dilutions of the lysates were made using diluents containing the biotinylated signal oligonucleotides. The solutions were then incubated for 30 minutes at ambient temperature with 4 nylon beads that had covalently immobilized 0.1 µg of Bg1 specific oligonucleotide probe (capture probe). The solid supports were washed with SDS/FW at ambient temperature and then incubated with 10 ng/ml of streptavidin/horseradish peroxidase (SA/HRP) conjugate in SDS/FW for 5 minutes at ambient temperature. The solid supports were washed with SDS/FW, FW, and then the presence of peroxidase was determined by incubating the bead for 20 minutes with the HRP substrate solution described above to form an insoluble product.

The beads were washed once with SDS/FW, wicked dry, and placed in an opaque white, round-bottom, 96 well microtiter plate (Dynatek Laboratories, Chantilly, Va.). The beads were read using a fluorometer (Fluoroskan II, Flow Laboratories, McLean, Va.) in which excitation was at 584 nanometers and emission was at 612 nanometers. The following results were obtained.

| Number Bg bacteria: | RFUs: |
| --- | --- |
| $1 \times 10^8$ | 3.06 |
| $9 \times 10^7$ | 3.07 |
| $3 \times 10^7$ | 3.32 |
| $1 \times 10^7$ | 3.95 |
| $3.3 \times 10^6$ | 5.57 |
| $1.1 \times 10^6$ | 7.42* |
| $3.7 \times 10^5$ | 10.29 |
| $1.2 \times 10^5$ | 13.08** |
| none (control) | 16.99 |
| none (control) | 17.18 |

*indicates the lowest level of visual detection
**indicates the lowest level of detection with a fluorometer The results described above indicate that the lowest level of visual detection occurred at $1.1 \times 10^5$ bacteria whereas the results from the fluorometry test yielded a sensitivity 9-fold better at $1.2 \times 10^5$ bacteria.

EXAMPLE 2

Example 2 describes the quantification of signal obtained in a typical sandwich assay format in which a target nucleic acid sequence is sequestered and then detected using a colorimetric insoluble enzymatic product obtained with a alkaline phosphatase system.

3M GnSCN lysis solution was used to lyse $1 \times 10^8$ Bacteroides gingivalis (Bg) cells in 250 microliter volume at 19° C. and then split into two equal volumes. The lysate was then heated to 65° C. for 5 minutes. A biotinylated 24-mer oligonucleotide probe complementary to conserved regions of bacterial 16 s rRNA (signal probe) was added to a final concentration of 100 nanograms per ml.

3-fold serial dilutions of the lysates were made using diluents in 3M GuSCN lysing and hybridization solution containing the biotinylated signal oligonucleotides. The solutions were then incubated for 30 minutes at ambient temperature with 2 to 4 nylon beads that had covalently immobilized 0.1 µg of Bg1 specific oligonucleotide probe (capture probe). The solid supports were washed with SDS/FW at ambient temperature and incubated with 10 ng/ml of streptavidin/alkaline phosphatase (SA/AP) conjugate in APB for 5 minutes at ambient temperature. The solid supports were then washed with APB, and then the presence of alkaline phosphatase was determined by incubating the filter with the TMNZ substrate solution described above for 4 hours to form an insoluble formazan product.

The beads were washed once with SDS/FW, wicked dry, and placed, one bead per well, in an opaque white, round-bottom, 96 well microtiter plate (Dynatek Laboratories, Chantilly, Va.). The beads were then read using a fluorometer (Fluoroskan II, Flow Laboratories, McLean, Va.) in which excitation was at 584 nanometers and emission was at 612 nanometers. The following results were obtained.

| Number Bg bacteria: | RFUs: |
| --- | --- |
| $1 \times 10^8$ | 2.15 |
| $9 \times 10^7$ | 2.14 |
| $3 \times 10^7$ | 2.22 |
| $1 \times 10^7$ | 2.36 |
| $3.3 \times 10^6$ | 2.76 |
| $1.1 \times 10^6$ | 4.45 |
| $3.7 \times 10^5$ | 7.03 |
| $1.2 \times 10^5$ | 8.79 |
| $4.0 \times 10^4$ | 10.87 |
| $1.3 \times 10^4$ | 12.67* |
| $4.3 \times 10^3$ | 14.32** |
| none (control) | 17.89 |
| none (control) | 17.55 |

*indicates the lowest level of visual detection
**indicates the lowest level of detection with a fluorometer The results described above indicate that the lowest level of visual detection occurred at $1.3 \times 10^4$ bacteria whereas the results from the fluorometry test yielded a sensitivity 3-fold better at $4.3 \times 10^3$ bacteria.

EXAMPLE 3

Example 3 demonstrates the ability of determining fluorescence of 4-methyl-umbelliferone in the presence of a solid support.

3M GnSCN lysis solution was used to lyse $1 \times 10^8$ cells of Actinobacillus actinomycetemcomitans (Aa), Bacteroides gingivalis (Bg), Bacteroides intermedius (Bi), Eikenella corrodens (Ec), Fusobacterium nucleatum (Fn), and Wolinella recta (Wr) in 100 microliter volumes at 19° C. The lysate was heated to 65° C. for 5 minutes. A biotinylated 24-mer oligonucleotide probe complementary to conserved regions of bacterial 16 s rRNA (signal probe) was added to a final concentration of 100 nanograms per ml.

5-fold serial dilutions of the lysates were made using diluents in 3M GuSCN lysing and hybridization solution containing the biotinylated signal oligonucleotides and $1 \times 10^8$ total cells of Aa, Bi, Ek, Fn, and Wr. The solutions were then incubated for 30 minutes at ambient temperature with 2 black nylon beads prepared by The Hoover Group (Sault St. Marie, Mich.) that had covalently immobilized 0.1 μg of Bgl specific oligonucleotide probe (capture probe).

The solid supports were washed with SDS/FW at ambient temperature, followed by washing with 0.5% Tween 20, 1 mM $MgCl_2$, 0.01M Tris-HCl pH 8.0 (APB) and then incubated with 0.4 ug/ml of streptavidin/alkaline phosphatase (SA/AP) conjugate in APB for 5 minutes at ambient temperature. The solid supports were washed 5 times with APB, TMNZ, and then the presence of alkaline phosphatase was determined by incubating the nylon beads with 150 microliters of 0.5 mM 4-methyl-umbelliferone phosphate in black microtiter well strips (Dynatek, Laboratories, Chantilly, Va.). Incubation was for 30 minutes at 37° C. The plates were directly read using a Fluoroskan II fluorometer (Flow Laboratories, McLean, Va.) with an excitation wavelength of 360 nm and an emission wavelength of 456 nm. The results are shown below.

| Cell number | Fluorescent signal Black beads | Native beads | Control |
|---|---|---|---|
| $1 \times 10^8$ | 1980 | 2760 | 1870 |
| $2 \times 10^7$ | 1250 | 2250 | 1140 |
| $4 \times 10^6$ | 680 | 1470** | 630 |
| $8 \times 10^5$ | 175 | 980 | 160 |
| $1.6 \times 10^5$ | 58 | 870 | 60 |
| $3.2 \times 10^4$ | 26 | 910 | 27 |
| $6.4 \times 10^3$ | 23** | 990 | 24** |
| control | 18 | 940 | 17 |

**indicates the lowest level of detection with a fluorometer

The results indicate that, in the 30 minute hybridization, $6.4 \times 10^3$ cells were detected using the black nylon beads as solid supports when the reading was made in the presence of the bead, whereas the native beads only allowed the detection of $4 \times 10^6$ cells when the reading was made in the presence of the bead. This is due to the very high intrinsic fluorescence associated with the native nylon beads (800-900 RFUs). The black nylon beads, which possess a very much lower intrinsic fluorescence (approximately 18 units), allowed the sensitive detection of Bg 16 s rRNA using a fluorescence based signal system.

The control, in which the solution was removed from the presence of the native bead and then read, indicated the same level, i.e. $6.4 \times 10^3$, of detection of bacteria as when the solution was read in the presence of the black bead.

EXAMPLE 4

Example 4 describes the dying of 3/32 inch nylon beads with different dyes and the resultant reduction of the intrinsic fluorescence of the nylon beads.

Approximately 500 mg of Mordant Brown 4, Cibacron Brilliant Red, Cibacron Brilliant Yellow, Reactive Black, Fast Blue BB, Mordant Orange, and Reactive Blue 2 was dissolved in 50 ml of 50% m-methyl-pyrrolidinone and 0.2M sodium Borate pH=8.3 and incubated with 1000 3/32 inch nylon beads for 24 hours at 19° C. and 1 hour at 65° C. The beads were then washed with 10 changes of 50 ml of 100% m-methyl-pyrrolidinone and 5 changes of 50 ml distilled water. The beads were dried under high vacuum for 25 hours. Eight beads from each color group were then placed in an opaque white, round-bottom, microtiter plate.

The plates were directly read using a Fluoroskan II fluorometer (Flow Laboratories, McLean, Va.) having an excitation wavelength of 360 nm and an emission wavelength of 456 nm. The results are shown below.

| Color: | Fluorescent signal RFUs: |
|---|---|
| Native (white) | 2000 |
| Mordant Brown 4 | 3.5 |
| Cibacron Brilliant Red | 110 |
| Cibacron Brilliant Yellow | 130 |
| Reactive Black | 2.5 |
| Fast Blue BB | 10 |
| Mordant Orange | 30 |
| Reactive Blue 2 | 3.0 |

Therefore, as shown above, dying the nylon bead significantly reduces the intrinsic fluorescence of the nylon bead, thereby rendering the beads compatible with fluorescence-based assays in the case of Mordant Brown 4, Reactive Black, Fast Blue BB, and Reactive Blue 2.

What is claimed is:

1. A method for detecting a member of a ligand pair comprising:
   contacting a target member of a ligand pair with a capture member of the ligand pair, said capture member immobilized on a solid support having intrinsic fluorescence, and said contacted pair in association with a colorimetric reporter;
   irradiating the solid support, said solid support attached to the ligand pair in association with the colorimetric reporter; and
   determining the resultant fluorescence.

2. The method according to claim 1 wherein the target member is an antibody and the capture member is an antigen, said antigen capable of binding with said antibody.

3. The method according to claim 1 wherein the target member is a first nucleic acid and the capture member is a second nucleic acid, said first nucleic acid and said second nucleic acid being complementary.

4. A method for nucleic acid detection comprising:
   contacting a target nucleic acid and a complementary capture nucleic acid probe, said capture probe immobilized on a solid support having intrinsic fluorescence, and said contacted target nucleic acid-capture probe complex in association with a colorimetric reporter;
   irradiating the solid support, said solid support attached to the hybridized capture probe-target nucleic acid complex; and
   determining the resultant fluorescence.

5. The method of claim 4 wherein the colorimetric reporter is attached to a signal nucleic acid probe, said signal probe complementary to the target nucleic acid.

6. The method of claim 5 wherein the solid support is selected from the group consisting of nylons, polyethylene, polyvinylchloride, polystyrene, polypropylene, acrylonitrile butadiene styrene, acrylics, acetals, polycarbonates, fluoroplastics, polyesters, phenolics, amino resins, epoxies, polyurethane, and silicones.

7. The method of claim 6 wherein the solid support is a nylon bead.

8. The method of claim 7 wherein the colorimetric reporter is an enzyme.

9. The method of claim 8 wherein the reporter enzyme is selected from the group consisting of horseradish peroxidase, alkaline phosphatase, and β-galactosidase.

10. A method for detecting a member of a ligand pair comprising:
   immobilizing a capture member of a ligand pair on a composition comprising a solid support having its intrinsic fluorescence quenched;
   contacting the target member of a ligand pair with the immobilized capture member of the ligand pair, said contacted pair in association with a fluorescent reporter;
   irradiating the solid support, said solid support attached to the ligand pair in association with the fluorescent reporter; and
   determining the resultant fluorescence.

11. The method according to claim 10 wherein the target member is a first nucleic acid and the capture member is a second nucleic acid, said first nucleic acid and said second nucleic acid being complementary.

12. The method according to claim 11 wherein resultant fluorescence is determined with a fluorometer.

13. A method for quantitating the amount of fluorescent quenching product deposited on a solid support having intrinsic fluorescence, comprising:
   (a) depositing a colorimetric reporter as a quenching product on a solid support having intrinsic fluorescence;
   (b) irradiating the solid support having the colorimetric reporter with a wavelength of light that produces fluorescence of the solid support; and then
   (c) comparing fluorescence of the solid support having the colorimetric reporter with fluorescence from solid support lacking the colorimetric reporter, thereby quantitating the amount of deposited colorimetric reporter.

14. The method of claim 13, wherein the solid support is nylon.

15. The method of claim 13, wherein the solid support has a diameter of about 0.01 inch to about 0.5 inch.

16. The method of claim 13, wherein the colorimetric reporter is an insoluble enzymatic product.

17. The method of claim 13, wherein the wavelength is about 240 nm to about 750 nm.

18. The method of claim 13, further including the step of separating the solid support having the colorimetric reporter from colorimetric reporter not deposited on the solid support after step (a) and before step (b).

* * * * *